(12) United States Patent
Devassy et al.

(10) Patent No.: US 12,179,176 B2
(45) Date of Patent: *Dec. 31, 2024

(54) CATALYST FOR PARAFFIN DEHYDROGENATION

(71) Applicant: SABIC GLOBAL TECHNOLOGIES B.V., Bergen op Zoom (NL)

(72) Inventors: Biju Maippan Devassy, Bangalore (IN); Rekha Mahadevaiah, Bangalore (IN); Prashant Kumar Raichur Krishtacharya, Bangalore (IN); Vinod Sankaran Nair, Bangalore (IN)

(73) Assignee: SABIC Global Technologies B.V., Bergen op Zoom (NL)

(*) Notice: Subject to any disclaimer, the term of this patent is extended or adjusted under 35 U.S.C. 154(b) by 188 days.

This patent is subject to a terminal disclaimer.

(21) Appl. No.: 17/282,929

(22) PCT Filed: Oct. 4, 2019

(86) PCT No.: PCT/IB2019/058497
§ 371 (c)(1),
(2) Date: Apr. 5, 2021

(87) PCT Pub. No.: WO2020/070723
PCT Pub. Date: Apr. 9, 2020

(65) Prior Publication Data
US 2021/0387167 A1    Dec. 16, 2021

Related U.S. Application Data

(60) Provisional application No. 62/742,229, filed on Oct. 5, 2018, provisional application No. 62/742,231, filed on Oct. 5, 2018.

(51) Int. Cl.
| | |
|---|---|
| *B01J 23/26* | (2006.01) |
| *B01J 21/04* | (2006.01) |
| *B01J 35/00* | (2024.01) |
| *B01J 35/10* | (2006.01) |
| *B01J 35/30* | (2024.01) |
| *B01J 35/61* | (2024.01) |
| *B01J 35/63* | (2024.01) |
| *B01J 37/00* | (2006.01) |
| *B01J 37/02* | (2006.01) |
| *B01J 37/04* | (2006.01) |
| *B01J 37/08* | (2006.01) |
| *C07C 5/333* | (2006.01) |

(52) U.S. Cl.
CPC .............. *B01J 23/26* (2013.01); *B01J 21/04* (2013.01); *B01J 35/30* (2024.01); *B01J 35/613* (2024.01); *B01J 35/615* (2024.01); *B01J 35/633* (2024.01); *B01J 37/0009* (2013.01); *B01J 37/0207* (2013.01); *B01J 37/04* (2013.01); *B01J 37/082* (2013.01); *C07C 5/3335* (2013.01); *C07C 2521/04* (2013.01); *C07C 2523/10* (2013.01); *C07C 2523/26* (2013.01)

(58) Field of Classification Search
CPC . B01J 23/26; B01J 21/04; B01J 35/002; B01J 35/1014; B01J 35/1019; B01J 35/1038; B01J 37/0009; B01J 37/0207; B01J 37/04; B01J 37/082; C07C 5/3335
See application file for complete search history.

(56) References Cited

U.S. PATENT DOCUMENTS

| | | | |
|---|---|---|---|
| 2,374,404 | A | 4/1945 | Ahlberg |
| 2,945,823 | A | 7/1960 | Cornelius et al. |
| 2,956,030 | A | 10/1960 | Cornelius et al. |
| 4,722,920 | A | 2/1988 | Kimura et al. |
| 5,266,548 | A | 11/1993 | Koradia et al. |
| 5,510,552 | A | 4/1996 | Dellinger et al. |
| 5,718,879 | A * | 2/1998 | Chopin ............... C01F 7/02 |
| | | | 423/628 |
| 6,007,700 | A | 12/1999 | Alario et al. |
| 6,248,688 | B1 | 6/2001 | Wu et al. |
| 6,429,167 | B1 | 8/2002 | Maeno et al. |
| 7,982,074 | B2 | 7/2011 | Rao et al. |
| 8,680,357 | B1 | 3/2014 | Rokicki et al. |
| 9,254,476 | B2 | 2/2016 | Ruettinger et al. |
| 9,415,378 | B2 | 8/2016 | Kauffman et al. |

(Continued)

FOREIGN PATENT DOCUMENTS

| | | |
|---|---|---|
| CN | 102019178 | 4/2011 |
| CN | 104128175 | 11/2014 |

(Continued)

OTHER PUBLICATIONS

Borisevich et al., "Dual Nanoparticle/Substrate Control of Catalytic Dehydrogenation" *Adv. Mater.* 2007, 19, 2129-2133.

(Continued)

*Primary Examiner* — Yong L Chu (74) *Attorney, Agent, or Firm* — Norton Rose Fulbright US LLP (57) ABSTRACT

Rare earth element containing catalysts for dehydrogenating paraffins and the methods of making the catalysts are disclosed. A rare earth modified alumina support in eta-alumina form, theta-alumina form, or combinations thereof is impregnated with chromium-containing solution. The chromium-impregnated support is then subjected to calcination processes. The produced catalyst contains the rare earth element, chromium, and alumina. The crush strength of the produced catalyst is greater than 0.4 daN/mm.

12 Claims, 3 Drawing Sheets

(56) References Cited

U.S. PATENT DOCUMENTS

| | | | |
|---|---|---|---|
| 2005/0054738 A1 | 3/2005 | Fraenkel | |
| 2005/0075243 A1 | 4/2005 | Fridman et al. | |
| 2005/0234137 A1 | 10/2005 | Espinoza et al. | |
| 2006/0047130 A1 | 3/2006 | Yeates et al. | |
| 2006/0149112 A1* | 7/2006 | Rokicki | C07C 5/3332 585/654 |
| 2006/0241325 A1 | 10/2006 | Komplin et al. | |
| 2015/0119590 A1 | 4/2015 | Li et al. | |
| 2021/0001316 A1* | 1/2021 | Devassy | B01J 37/0236 |

FOREIGN PATENT DOCUMENTS

| | | | |
|---|---|---|---|
| CN | 105817258 | 8/2016 | |
| CN | 105817258 B * | 7/2018 | B01J 29/0341 |
| EP | 0947247 | 10/1999 | |
| FR | 2187887 | 11/1975 | |
| GB | 942944 | 11/1963 | |
| WO | WO 2004/060839 | 7/2004 | |
| WO | WO 2014/046659 | 3/2014 | |
| WO | WO 2019/180518 | 9/2019 | |

OTHER PUBLICATIONS

International Search Report and Written Opinion issued in Corresponding PCT Application No. PCT/IB2019/058497, dated Dec. 20, 2019.

Koryabkina et al., "Synthesis of a mechanically strong and thermally stable alumina support for catalysts used in combustion processes" *Catalysis Today* 1996, 29, 427-431.

Lu et al., "Effect of Lanthanum and Cerium Modifiers on Properties of Alumina" *Chinese Journal of Catalysis* 2003, 24(8):574-578. (English abstract provided).

Oberlander, Richard K. "Aluminas for Catalysts—Their Preparation and Properties" Chapter 4, *Applied Industrial Catalysis*, vol. 3, Academic Press, Inc., 1984.

Oudet et al., "Thermal Stabilization of Transition Alumina by Structural Coherence with LnA103 (Ln = La, Pr, Nd)" *Journal of Catalysis* 1988, 114, 112-120.

Patel et al., "Structural Effects of Lanthanide Dopants on Alumina" *Scientific Reports* 2017, 7(1), 9 pages.

Rashkeev et al., "Transition metal atoms on different alumina phases: The role of subsurface sites on catalytic activity" *Phys. Rev. B* 2003, 67, 115414, 4 pages.

Ryashentseva et al., "The role of oxides in an aluminum-lanthanum-chromium-potassium catalyst in the interaction of $C_4$-hydrocarbons and hydrogen sulfide" *Russ Chem Bull* 1972, 21: 1483-1488.

Wefers, Karl and Chanakya Misra. *Oxides and hydroxides of aluminum; Alcoa Technical Paper No. 19, revised.* Alcoa laboratories, 1987.

Xiaoli et al., "Study on thermal stability of alumina for selective hydrogenation catalysts" *Petrochemical Technology & Application* 2011 (English abstract provided).

Office Action issued in counterpart European Patent Application No. 19794657.7 dated Oct. 15, 2024.

* cited by examiner

CATALYST FOR PARAFFIN DEHYDROGENATION

CROSS REFERENCE TO RELATED APPLICATIONS

This application is a national phase under 35 U.S.C. § 371 of International Application No. PCT/IB2019/058497, filed Oct. 4, 2019, which claims the benefit of priority to U.S. Provisional Patent Application Ser. No. 62/742,229 filed Oct. 5, 2018, and U.S. Provisional Patent Application Ser. No. 62/742,231 filed Oct. 5, 2018, the entire contents of each of which are hereby incorporated by reference in their entirety.

FIELD OF INVENTION

The present invention generally relates to catalysts for paraffin dehydrogenation. More specifically, the present invention relates to a paraffin dehydrogenation catalyst with modified support for increased crush strength.

BACKGROUND OF THE INVENTION

Alkane dehydrogenation is a process used for producing a variety of alkene products. Examples of these alkene products include isobutylene used for producing methyl tert-butyl ether (MTBE) and propylene used for polypropylene production. Currently, most commercially available alkane dehydrogenation technologies, including Süd-Chemie CATOFIN® process, UOP's Oleflex® process, Phillips' Star™ process, and the Snamprogetti-Yarsintez process, use fixed bed or fluidized bed reactors with various types of catalysts.

Chromia supported on alumina is one of the most common catalysts used for alkane dehydrogenation. While this type of catalyst has been used for decades, there are a few drawbacks associated with them when used in fixed bed reactors. First of all, the thermal stability of chromium based catalysts is relatively low. Due to high operating temperatures in both online mode and regeneration mode of the alkane dehydrogenation process, the low thermal stability of the catalyst has a significant negative impact on the life expectancy of the catalyst bed, resulting in frequent replacing of the catalysts. Secondly, currently available chromia based catalysts generally lack sufficient mechanical strength to support their own weight and endure the turbulence of process streams of the alkane dehydrogenation process. During the dehydrogenation process, the mechanical strength of the catalyst gradually reduces to a point that the catalyst has to be discarded even though the metal elements in the catalysts are still active to catalyze the dehydrogenation reaction, resulting in waste of active metals in the catalyst. Therefore, the efficiency of conventional catalysts in alkane dehydrogenation processes is relatively low.

Overall, while catalysts for alkane dehydrogenation exist, the need for improvements in this field persists in light of at least the aforementioned drawbacks.

BRIEF SUMMARY OF THE INVENTION

A solution to at least some of the above-mentioned problems associated with the chromium based catalysts has been discovered. The solution resides in a catalyst having a rare earth element modified support material and a method of producing the catalyst that includes multiple calcination steps. Notably, the chromia-alumina catalyst made by the method shows increased crush strength compared to conventional chromium based dehydrogenation catalysts. Furthermore, the catalyst made by the method shows increased thermal stability over conventional chromium based dehydrogenation catalyst. Overall, the catalyst, according to embodiments of the inventive method, has an increased life expectancy over the conventional dehydrogenation catalyst, resulting in reduced production cost. Therefore, the catalyst and the methods of the present invention provide a technical solution to at least some of the problems associated with the currently available catalysts for dehydrogenating alkanes.

Embodiments of the invention include a paraffin dehydrogenation catalyst having an improved crush strength. The paraffin dehydrogenation catalyst is produced by a process comprising providing a rare earth element modified alumina support in eta-alumina form, theta-alumina form, or combinations thereof. The process further comprises impregnating the rare earth element modified alumina support in eta-alumina form, theta alumina form, or combinations thereof with a chromium-containing solution to produce a second support. The process further includes drying the second support and calcining the dried second support to obtain the paraffin dehydrogenation catalyst. The paraffin dehydrogenation catalyst has a crush strength greater than about 0.4 daN/mm. The paraffin dehydrogenation catalyst contains an oxide of a rare earth element in a range between 0.5-5% by weight. In embodiments of the invention, the oxide of the rare earth element may include lanthanum oxide.

Embodiments of the invention include a paraffin dehydrogenation catalyst having an improved crush strength. The paraffin dehydrogenation catalyst is produced by a process comprising providing a rare earth element modified alumina support in eta-alumina form, theta-alumina form, or combinations thereof (step (a)). The process further comprises impregnating the rare earth element modified alumina support with a chromium-containing solution to produce a second support. The process further includes drying the second support and calcining the dried second support to obtain the paraffin dehydrogenation catalyst. The paraffin dehydrogenation catalyst has a crush strength greater than about 0.4 daN/mm. The paraffin dehydrogenation catalyst contains an oxide of a rare earth element in a range between 0.5-5%, or 0.8-4%, or 0.5-1%, by weight. In embodiments of the invention, the oxide of the rare earth element may include lanthanum oxide. The providing in step (a) includes providing an eta-alumina support. The providing in step (a) further includes impregnating the eta-alumina support with a rare earth element-containing solution to produce a first support. The providing in step (a) further still includes drying the first support and calcining the dried first support to obtain a rare earth element modified alumina support in eta-alumina form, theta-alumina form, or combinations thereof.

Embodiments of the invention include a paraffin dehydrogenation catalyst having an improved crush strength. The paraffin dehydrogenation catalyst is produced by a process comprising providing a rare earth element modified alumina support in eta-alumina form, theta-alumina form, or combinations thereof (step (a)). The process further comprises impregnating the rare earth element modified alumina support with a chromium-containing solution to produce a second support. The process further includes drying the second support and calcining the dried second support to obtain the paraffin dehydrogenation catalyst. The paraffin dehydrogenation catalyst has a crush strength greater than about 0.4 daN/mm. The paraffin dehydrogenation catalyst contains an oxide of a rare earth element in a range between 0.5-5%, or 0.8-4%, or 0.5-1%, by weight. In embodiments of the invention, the oxide of the rare earth element may include lanthanum oxide. The providing in step (a) includes providing a precursor of an eta-alumina support; contacting the precursor with a rare earth element-containing solution to produce a contacted precursor; shaping the contacted precursor of an eta-alumina support; drying the contacted precursor and calcining the dried contacted precursor to produce a rare earth element modified alumina support in eta-alumina form, theta-alumina form, or combinations thereof.

The following includes definitions of various terms and phrases used throughout this specification.

The phrases "rare earth metal," "rare earth additive," and "rare earth element" are used interchangeably herein.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, paraffin dehydrogenation catalysts used in fixed bed reactors generally have low stability and limited mechanical strength, which lead to low life expectancy for the catalysts and high production costs resulting from frequently replacing the catalysts. The present invention provides a solution to these problems. The solution is premised on a catalyst that includes a rare earth element modified alumina support in eta-alumina form, theta-alumina form, or combinations thereof. The catalyst is produced via multiple calcination steps and includes chromium and a rare earth element on the alumina support in eta-alumina form, theta-alumina form, or combinations thereof. The stability and the mechanical strength of this catalyst is improved over the conventional chromium based dehydrogenation catalysts, resulting in reduced production cost for dehydrogenating paraffin. These and other non-limiting aspects of the present invention are discussed in further detail in the following sections.

A. Methods of Producing Paraffin Dehydrogenation Catalyst

Figure 1:
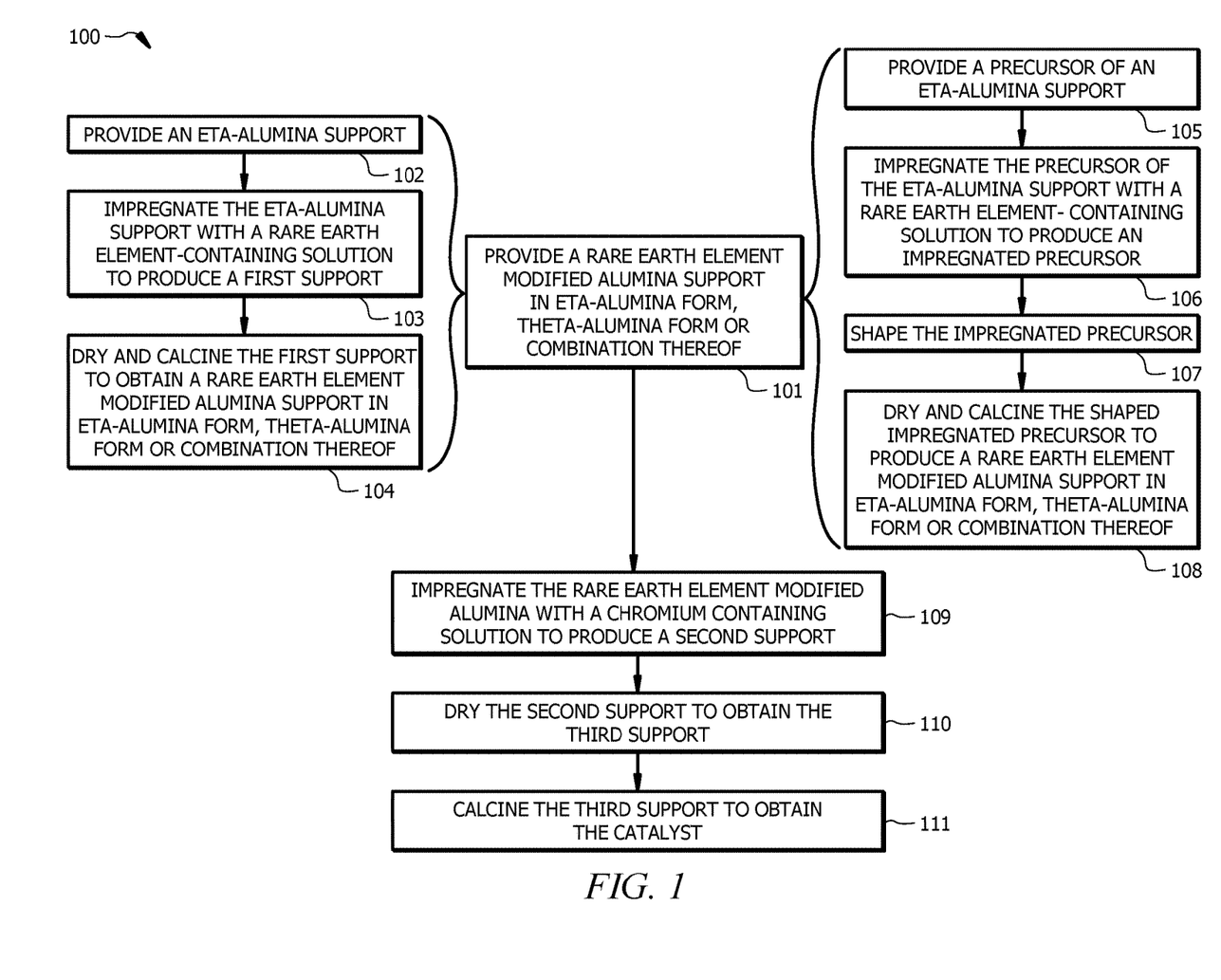
FIG. 1 shows a schematic flowchart of a method of producing a paraffin dehydrogenation catalyst, according to embodiments of the invention.

In embodiments of the invention, the catalyst for dehydrogenating paraffin can include a rare earth element modified alumina support in eta-alumina form, theta-alumina form, or combinations thereof. With reference to FIG. 1, a schematic flowchart is shown of process 100 for producing a paraffin dehydrogenation catalyst having an improved crush strength compared to conventional paraffin dehydrogenation catalysts.

According to embodiments of the invention, process 100 may include providing a rare earth element modified alumina support in eta-alumina form, theta-alumina form, or combinations thereof (step (a)), as shown in block 101. In embodiments of the invention, the rare earth element may include lanthanum, cerium, neodymium, or combinations thereof.

In embodiments of the invention, the providing step in block 101 may include providing an eta-alumina support, as shown in block 102. The providing step in block 101 may further include impregnating the eta-alumina support with a rare earth element-containing solution to produce a first support, as shown in block 103. In embodiments of the invention, the providing step in block 101 may further still include a heating step comprising drying the first support and calcining the dried first support to obtain the rare earth element modified alumina support in eta-alumina form, theta-alumina form, or combinations thereof, as shown in block 104.

In embodiments of the invention, the eta-alumina support in block 102 may include extruded eta-alumina pellets. In embodiments of the invention, non-limiting examples of the rare earth element containing solution include a solution selected from the group consisting of lanthanum, cerium, neodymium, or combinations thereof. According to embodiments of the invention, the drying temperature in block 104 may be in a range of 70 to 150° C. and all ranges and values there between including 70 to 74° C., 74 to 78° C., 78 to 82° C., 82 to 86° C., 86 to 90° C., 90 to 94° C., 94 to 98° C., 98 to 102° C., 102 to 106° C., 106 to 110° C., 110 to 114° C., 114 to 118° C., 118 to 122° C., 122 to 126° C., 126 to 130° C., 130 to 134° C., 134 to 138° C., 138 to 142° C., 142 to 146° C., and 146 to 150° C. The calcining in block 104 may be performed at a temperature in a range of 700 to 1000° C. and all ranges and values there between including 700 to 715° C., 715 to 730° C., 730 to 745° C., 745 to 760° C., 760 to 775° C., 775 to 790° C., 790 to 805° C., 805 to 820° C., 820 to 835° C., 835 to 850° C., 850 to 865° C., 865 to 880° C., 880 to 895° C., 895 to 910° C., 910 to 925° C., 925 to 940° C., 940 to 955° C., 955 to 970° C., 970 to 985° C., and 985 to 1000° C. The temperature ramp of the calcining in block 104 may be in a range of 0.5 to 10° C./min and all ranges and values there between including ranges of 0.5 to 1° C./min, 1 to 1.5° C./min, 1.5 to 2.0° C./min, 2.0 to 2.5° C./min, 2.5 to 3.0° C./min, 3.0 to 3.5° C./min, 3.5 to 4.0° C./min, 4.0 to 4.5° C./min, 4.5 to 5.0° C./min, 5.0 to 5.5° C./min, 5.5 to 6.0° C./min, 6.0 to 6.5° C./min, 6.5 to 7.0° C./min, 7.0 to 7.5° C./min, 7.5 to 8.0° C./min, 8.0 to 8.5° C./min, 8.5 to 9.0° C./min, and 9.0 to 10.0° C./min. The calcination duration in block 104 may be in a range of 0.5 to 4 hours and all ranges and values there between. In embodiments of the invention, the calcining in block 104 may be performed in an atmospheric environment comprising oxygen, nitrogen, steam, or combinations thereof.

Additionally or alternatively, in embodiments of the invention, the providing step in block 101 may include providing a precursor of an eta-alumina support, as shown in block 105. The providing step in block 101 may further include contacting the precursor with a rare earth element-containing solution to produce a contacted precursor, as shown in block 106. The providing step in block 101 may further include shaping the contacted precursor of an eta-alumina support to produce a shaped contacted precursor, as shown in block 107. In embodiments of the invention, the precursor is contacted with the at least one rare earth additive at block 106 before the shaping step of block 107. The providing step in block 101 may further still include a heating step comprising drying the shaped contacted precursor and calcining the dried shaped contacted precursor to produce a rare earth element modified alumina support in eta-alumina form, theta-alumina form, or combinations thereof, as shown in block 108.

In embodiments of the invention, the precursor of the eta-alumina support may include bayerite, rho alumina, gel alumina (see Oxides and Hydroxides of Aluminum, Alcoa Technical Paper No. 19, revised by Karl Wefers and Chanakya Misra, Alcoa Laboratories 1987), or combinations thereof. In embodiments of the invention, non-limiting examples of the rare earth element containing solution include solution of lanthanum, cerium, neodymium, or combinations thereof. According to embodiments of the invention, the shaping in block 107 may include extrusion, pelleting, or combinations thereof. In embodiments of the invention, the drying in block 108 may include a drying temperature in a range of 70 to 150° C. and all ranges and values there between. In embodiments of the invention, the calcining in block 108 may be performed at a temperature in a range of 700 to 1000° C. and all ranges and values there between. The temperature ramp of the calcining in block 108 may be in a range of 0.5 to 10° C./min and all ranges and values there between including ranges of 0.5 to 10° C./min and all ranges and values there between including ranges of 0.5 to 1° C./min, 1 to 1.5° C./min, 1.5 to 2.0° C./min, 2.0 to 2.5° C./min, 2.5 to 3.0° C./min, 3.0 to 3.5° C./min, 3.5 to 4.0° C./min, 4.0 to 4.5° C./min, 4.5 to 5.0° C./min, 5.0 to 5.5° C./min, 5.5 to 6.0° C./min, 6.0 to 6.5° C./min, 6.5 to 7.0° C./min, 7.0 to 7.5° C./min, 7.5 to 8.0° C./min, 8.0 to 8.5° C./min, 8.5 to 9.0° C./min, and 9.0 to 10.0° C./min. The calcination duration in block 108 may be in a range of 0.5 to 4 hours and all ranges and values there between. In embodiments of the invention, the calcining in block 108 may be performed in an atmospheric environment comprising oxygen, nitrogen, steam, or combinations thereof.

In embodiments of the invention, process 100 may further include impregnating the rare earth element modified alumina support in eta-alumina form, theta-alumina form, or combinations thereof in a chromium containing solution to produce a second support, as shown in block 109. In embodiments of the invention, the chromium-containing solution may include a chromium compound. Non-limiting examples of the chromium compound may include chromium hydroxide, sodium chromate, sodium dichromate, chromium nitrate, chromium acetate, chromium trioxide, and combinations thereof. Preferred chromium compounds are water-soluble chromium compounds. In embodiments of the invention, the impregnating step at block 109 further includes impregnating the rare earth element modified alumina support with at least one alkali metal compound before or after the rare earth element modified alumina support is impregnated by the chromium-containing solution. In embodiments of the invention, a solution comprising the at least one alkali metal and the chromium compound can be used to impregnate the rare earth element modified alumina support. Exemplary alkali metal compounds include a sodium compound, a potassium compound, a rubidium compound, a cesium compound, and combinations thereof. In embodiments of the invention, the impregnating at block 109 comprises impregnating to a chromium compound loading of up to and including 50%.

In embodiments of the invention, process 100 may further include drying the second support to obtain the third support, as shown in block 110. In embodiments of the invention, the drying temperature in block 110 may be in a range of 70 to 150° C. and all ranges and values there between including ranges of 70 to 74° C., 74 to 78° C., 78 to 82° C., 82 to 86° C., 86 to 90° C., 90 to 94° C., 94 to 98° C., 98 to 102° C., 102 to 106° C., 106 to 110° C., 110 to 114° C., 114 to 118° C., 118 to 122° C., 122 to 126° C., 126 to 130° C., 130 to 134° C., 134 to 138° C., 138 to 142° C., 142 to 146° C., and 146 to 150° C.

According to embodiments of the invention, process 100 may further include calcining the third support to obtain the catalyst, as shown in block 111. Upon calcination at block 111, the chromium compound is largely converted to chromium (III) oxide ($Cr_2O_3$). In embodiments of the invention, the calcination temperature in block 111 may be in a range of 650 to 850° C. and all ranges and values there between including ranges of 650 to 660° C., 660 to 670° C., 670 to 680° C., 680 to 690° C., 690 to 700° C., 700 to 710° C., 710 to 720° C., 720 to 730° C., 730 to 740° C., 740 to 750° C., 750 to 760° C., 760 to 770° C., 770 to 780° C., 780 to 790° C., 790 to 800° C., 800 to 810° C., 810 to 820° C., 820 to 830° C., 830 to 840° C., and 840 to 850° C. A temperature ramp of the calcining in block 111 may be in a range of 0.5 to 10° C./min and all ranges and values there between including ranges of 0.5 to 1° C./min, 1 to 1.5° C./min, 1.5 to 2.0° C./min, 2.0 to 2.5° C./min, 2.5 to 3.0° C./min, 3.0 to 3.5° C./min, 3.5 to 4.0° C./min, 4.0 to 4.5° C./min, 4.5 to 5.0° C./min, 5.0 to 5.5° C./min, 5.5 to 6.0° C./min, 6.0 to 6.5° C./min, 6.5 to 7.0° C./min, 7.0 to 7.5° C./min, 7.5 to 8.0° C./min, 8.0 to 8.5° C./min, 8.5 to 9.0° C./min, and 9.0 to 10.0° C./min. In embodiments of the invention, the calcination duration in block 111 may be in a range of 0.5 to 4 hours and all ranges and values there between including ranges of 0.5 to 1 hour, 1 to 1.5 hours, 1.5 to 2.0 hours, 2.0 to 2.5 hours, 2.5 to 3.0 hours, 3.0 to 3.5 hours, and 3.5 to 4.0 hours. In embodiments of the invention, the calcining in block 111 may be performed in an atmospheric e.g. a second atmospheric environment comprising air, carbon dioxide, steam, or combinations thereof.

In embodiments of the invention, the paraffin dehydrogenation catalyst produced via process 100 may include 5 to 40 wt. % chromium oxide, preferably 13 to 28 wt. % and all ranges and values there between including ranges of 13 to 14 wt. %, 14 to 15 wt. %, 15 to 16 wt. %, 16 to 17 wt. %, 17 to 18 wt. %, 18 to 19 wt. %, 19 to 20 wt. %, 20 to 21 wt. %, 21 to 22 wt. %, 22 to 23 wt. %, 23 to 24 wt. %, 24 to 25 wt. %, 25 to 26 wt. %, 26 to 27 wt. %, and 27 to 28 wt. %. The paraffin dehydrogenation catalyst produced via process 100 may further include 0.1 to 10 wt. %, preferably 1 to 5 wt. % oxides of at least one rare earth metal and all ranges and values there between including ranges of 1 to 1.2 wt. %, 1.2 to 1.4 wt. %, 1.4 to 1.6 wt. %, 1.6 to 1.8 wt. %, 1.8 to 2.0 wt. %, 2.0 to 2.2 wt. %, 2.2 to 2.4 wt. %, 2.4 to 2.6 wt. %, 2.6 to 2.8 wt. %, 2.8 to 3.0 wt. %, 3.0 to 3.2 wt. %, 3.2 to 3.4 wt. %, 3.4 to 3.6 wt. %, 3.6 to 3.8 wt. %, 3.8 to 4.0 wt. %, 4.0 to 4.2 wt. %, 4.2 to 4.4 wt. %, 4.4 to 4.6 wt. %, 4.6 to 4.8 wt. %, and 4.8 to 5.0 wt. %. In embodiments of the invention, the paraffin dehydrogenation catalyst produced via process 100 may further include 0.1 to 5 wt. % of at least one alkali metal and all ranges and values there between, including ranges of 0.1 to 0.2 wt. %, 0.2 to 0.3 wt. %, 0.3 to 0.4 wt. %, 0.4 to 0.5 wt. %, 0.5 to 0.6 wt. %, 0.6 to 0.7 wt. %, 0.7 to 0.8 wt. %, 0.8 to 0.9 wt. %, 0.9 to 1.0 wt. %, 1 to 1.2 wt. %, 1.2 to 1.4 wt. %, 1.4 to 1.6 wt. %, 1.6 to 1.8 wt. %, 1.8 to 2.0 wt. %, 2.0 to 2.2 wt. %, 2.2 to 2.4 wt. %, 2.4 to 2.6 wt. %, 2.6 to 2.8 wt. %, 2.8 to 3.0 wt. %, 3.0 to 3.2 wt. %, 3.2 to 3.4 wt. %, 3.4 to 3.6 wt. %, 3.6 to 3.8 wt. %, 3.8 to 4.0 wt. %, 4.0 to 4.2 wt. %, 4.2 to 4.4 wt. %, 4.4 to 4.6 wt. %, 4.6 to 4.8 wt. %, and 4.8 to 5.0 wt. %. In embodiments of the invention, the catalyst weight balance is eta-alumina, theta-alumina, or a combinations thereof.

In embodiments of the invention, the paraffin dehydrogenation catalyst has a surface area in a range of 60 to 120 $m^2/g$ and all ranges and values there between including ranges of 60 to 63 $m^2/g$, 63 to 66 $m^2/g$, 66 to 69 $m^2/g$, 69 to 72 $m^2/g$, 72 to 75 $m^2/g$, 75 to 78 $m^2/g$, 78 to 81 $m^2/g$, 81 to 84 $m^2/g$, 84 to 87 $m^2/g$, 87 to 90 $m^2/g$, 90 to 93 $m^2/g$, 93 to 96 $m^2/g$, 96 to 99 $m^2/g$, 99 to 102 $m^2/g$, 102 to 105 $m^2/g$, 105 to 108 $m^2/g$, 108 to 111 $m^2/g$, 111 to 114 $m^2/g$, 114 to 117 $m^2/g$, and 117 to 120 $m^2/g$. The pore volume (nitrogen adsorption-desorption) of the paraffin dehydrogenation catalyst may be in a range of 0.1 to 0.4 $cm^3/g$ and all ranges and values there between including ranges of 0.1 to 0.15 $cm^3/g$, 0.15 to 0.20 $cm^3/g$, 0.20 to 0.25 $cm^3/g$, 0.25 to 0.30 $cm^3/g$, 0.30 to 0.35 $cm^3/g$, and 0.35 to 0.40 $cm^3/g$. In embodiments of the invention, the paraffin dehydrogenation catalyst has a bulk density in a range of 0.8 to 1.2 g/ml and all ranges and values there between including ranges of 0.8 to 0.85 g/ml, 0.85 to 0.90 g/ml, 0.90 to 0.95 g/ml, 0.95 to 1.0 g/ml, 1.05 to 1.10 g/ml, 1.10 to 1.15 g/ml, and 1.15 to 1.20 g/ml. In embodiments of the invention, the paraffin dehydrogenation catalyst may have a crush strength greater than or equal to about 0.4 daN/mm.

B. Methods for Dehydrogenating Paraffin

Figure 2:
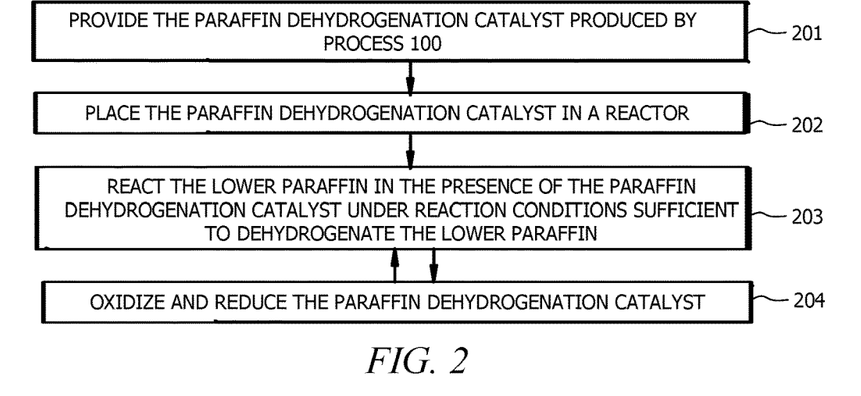
FIG. 2 shows a schematic flowchart of a method of dehydrogenating a lower paraffin using a catalyst, according to embodiments of the invention.

As shown in FIG. 2, embodiments of the invention include method 200 for dehydrogenating a lower paraffin. In embodiments of the invention, the lower paraffin may include ethane, propane, butane, isobutane, pentane, or combinations thereof. Method 200 may be implemented by the paraffin dehydrogenation catalyst produced via process 100, as shown in FIG. 1. According to embodiments of the invention, as shown in block 201, method 200 may include providing the paraffin dehydrogenation catalyst produced via process 100.

In embodiments of the invention, method 200 may further include placing the paraffin dehydrogenation catalyst in a reactor, as shown in block 202. According to embodiments of the invention, the reactor may be a fixed bed reactor. In embodiments of the invention, a fixed catalyst bed in the reactor may include particles of the paraffin dehydrogenation catalyst having a diameter in a range of 2 to 4 mm and all ranges and values there between including ranges of 2 to 2.1 mm, 2.1 to 2.2 mm, 2.2 to 2.3 mm, 2.3 to 2.4 mm, 2.4 to 2.5 mm, 2.5 to 2.6 mm, 2.6 to 2.7 mm, 2.7 to 2.8 mm, 2.8 to 2.9 mm, 2.9 to 3.0 mm, 3.0 to 3.1 mm, 3.1 to 3.2 mm, 3.2 to 3.3 mm, 3.3 to 3.4 mm, 3.4 to 3.5 mm, 3.5 to 3.6 mm, 3.6 to 3.7 mm, 3.7 to 3.8 mm, 3.8 to 3.9 mm, and 3.9 to 4.0 mm In embodiments of the invention, the fixed catalyst bed in the reactor may further include alpha-alumina, a heat generating material, or combinations thereof.

In embodiments of the invention, method 200 may further include reacting the lower paraffin in the presence of the paraffin dehydrogenation catalyst under reaction conditions sufficient to dehydrogenate the lower paraffin, as shown in block 203. In embodiments of the invention, the reaction conditions in block 203 may include a reaction temperature of 400 to 800° C. and all ranges and values there between including ranges of 400 to 420° C., 420 to 440° C., 440 to 460° C., 460 to 480° C., 480 to 500° C., 500 to 520° C., 520 to 540° C., 540 to 560° C., 560 to 580° C., 580 to 600° C., 600 to 620° C., 620 to 640° C., 640 to 660° C., 660 to 680° C., 680 to 700° C., 700 to 720° C., 720 to 740° C., 740 to 760° C., 760 to 780° C., and 780 to 800° C. The reaction conditions in block 203 may further include a reaction pressure of 0.2 to 1 bar and all ranges and values there between including 0.3 bar, 0.4 bar, 0.5 bar, 0.6 bar, 0.7 bar, 0.8 bar, and 0.9 bar. The reaction conditions may further include a gas and/or weight hourly space velocity of 300 to 800 hr$^{-1}$ and all ranges and values there between including ranges of 300 to 320 hr$^{-1}$, 320 to 340 hr$^{-1}$, 340 to 360 hr$^{-1}$, 360 to 380 hr$^{-1}$, 380 to 400 hr$^{-1}$, 400 to 420 hr$^{-1}$, 420 to 440 hr$^{-1}$, 440 to 460 hr$^{-1}$, 460 to 480 hr$^{-1}$, 480 to 500 hr$^{-1}$, 500 to 520 hr$^{-1}$, 520 to 540 hr$^{-1}$, 540 to 560 hr$^{-1}$, 560 to 580 hr$^{-1}$, 580 to 600 hr$^{-1}$, 600 to 620 hr$^{-1}$, 620 to 640 hr$^{-1}$, 640 to 660 hr$^{-1}$, 660 to 680 hr$^{-1}$, 680 to 700 hr$^{-1}$, 700 to 720 hr$^{-1}$, 720 to 740 hr$^{-1}$, 740 to 760 hr$^{-1}$, 760 to 780 hr$^{-1}$, and 780 to 800 hr$^{-1}$. In embodiments of the invention, the reacting at block 203 is performed at a gas hourly space velocity in a range of 250 to 750 mlh$^{-1}$g$^{-1}$, preferably from 350 to 650 mlh$^{-1}$g$^{-1}$, more preferably from 400 to 600 mlh$^{-1}$g$^{-1}$.

As shown in block 204, method 200 may further comprise the steps of oxidizing and reducing the paraffin dehydrogenation catalyst. In embodiments of the invention, the oxidizing and reducing at block 204 and the reacting at block 203 are cyclically repeated. An inert gas such as steam or nitrogen may be passed through the reactor between any or all of the oxidizing, reducing, and reacting steps.

Although embodiments of the present invention have been described with reference to blocks of FIGS. 1 and 2, it should be appreciated that operation of the present invention is not limited to the particular blocks and/or the particular order of the blocks illustrated in FIGS. 1 and 2. Accordingly, embodiments of the invention may provide functionality as described herein using various blocks in a sequence different than that of FIGS. 1 and 2.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Comparative Example 1

(Preparation of Catalyst without Rare Earth Element, Comparative Example)

Eta-alumina extrudates (about 3.1 mm×8.9 mm) with a surface area of 335 m$^2$/g were used for catalyst preparation. A hundred grams of alumina support was heat-treated (calcined) in presence of air in a tubular furnace at 800° C. for 2 hours at an air flow rate of 21 ml/min. The calcined extrudates were used for catalyst preparation by an incipient wetness impregnation method. The water pore volume of the extrudates (surface area modified by calcination) were measured by taking 5 gram support and titrating it against demineralized water. The end point was the point at which the extrudates adhered to the surface of the glassware. The measurement water pore volume was determined to be 0.39±0.1 cm$^3$/g.

About 100 ml chromium (VI) oxide (CrO$_3$) stock solution was prepared by dissolving 114 g of CrO$_3$ in water. The impregnation solution was prepared by dissolving 0.77 g of NaOH in 17.4 mL of the chromium stock solution. The extrudates were dried at 120° C. for 2 hours prior to chromium impregnation.

The impregnation was carried out by contacting the impregnation solution with 44.4 g of heat treated and dried alumina support at room temperature. The impregnated alumina support was then kept at room temperature for 2 hours and then dried at 120° C. for 12 hours.

The dried sample was then calcined at 650° C. for 2 hours under air (flow rate, 240±5 ml/min), followed by calcining at 750° C. for 4 hours under 80% air and 20% steam environment (total flow rate 240±5 ml/g/hr). After calcination the catalyst was cooled under air then stored in an air-tight container. The final calculated composition of the catalyst was 25 wt. % Cr$_2$O$_3$ and 1 wt. % Na$_2$O, with the balance corresponding to Al$_2$O$_3$.

Example 2

(Preparation of a Rare Earth Metal-Containing Catalyst)

Eta-alumina extrudates (~3.1 mm×~8.9 mm) having a surface area of 335 m$^2$/g were used for catalyst preparation. This support was pretreated in air at 120° C. for 2 hrs. 4.78 g La(NO$_3$)$_3$·6H$_2$O was dissolved in 22.6 ml water and impregnated on 58 g of eta-alumina. This La$_2$O$_3$-impregnated material was kept at room temperature for 2 hours, dried at 120° C. for 12 hours, and calcined in the presence of air in a tubular furnace at 800° C. for 2 hours (air flow 21 ml/min). The calcined extrudates were used for catalyst preparation by an incipient wetness impregnation method.

The water pore volume of the calcined extrudates was measured by taking 5 g of support and titrating it against demineralized water. The end point was the point at which the extrudates adhered to the surface of the glassware. The measurement water pore volume was determined to be 0.39±0.1 cm$^3$/g.

100 ml of a chromium (VI) oxide (CrO$_3$) stock solution was prepared by dissolving 114 g of CrO$_3$ in water. The impregnation solution was prepared by dissolving 0.77 g of NaOH in 17.4 mL of the chromium stock solution.

The alumina was dried at 120° C. for 2 hours prior to chromium impregnation. The impregnation was carried out by contacting the impregnation solution with 44.4 g of heat treated and dried alumina support at room temperature. The impregnated alumina support was kept at room temperature for 2 hours then dried at 120° C. for 12 hours. The dried sample was then calcined at 650° C. for 2 hours under air (flow rate, 240±5 ml/min), then at 750° C. for 4 hours under 80% air and 20% steam (total flow rate 240±5 ml/g/hr). After calcination, the catalyst was cooled under air then stored in an air-tight container. The final calculated composition of the catalyst was 25 wt. % Cr$_2$O$_3$, 3 wt. % La$_2$O$_3$, and 1 wt. % Na$_2$O, with the balance corresponding to Al$_2$O$_3$.

Example 3

(Catalysts Testing)

Crush Strength Test of the Catalysts

The radial crush strength of the catalysts prepared in Examples 1 and 2 were measured. About 50 g of catalyst was dried for 2 hours in an oven at 300° C. After cooling the catalysts in a desiccator, 30 extrudates were used. Each extrudate was subjected to an increasing load up to breaking point. The force applied to the extrudate at the moment of break is determined in decanewton (daN) and the results for the crush strength are expressed in daN/mm and shown in Tables 1 and 2.

TABLE 1

Crush strength of the catalyst prepared using method in Example 1

| | Comparative Example 1 | | | |
|---|---|---|---|---|
| | Min value | Average value | Maximum value | Std Dev |
| Nominal Dia (mm) | 2.8 | 3.07 | 3.27 | 0.12 |
| Crushing Dia (mm) | 2.69 | 2.96 | 3.22 | 0.14 |
| Crush Strength (daN) | 1.6 | 2.93 | 4.82 | 0.92 |
| Slope (daN/mm) | 1.36 | 41.7 | 85.57 | 24.49 |
| Crushing strength (daN/mm) | 0.23 | 0.41 | 0.83 | 0.15 |
| Force rate (daN/s) | 0.1 | 0.42 | 0.86 | 0.24 |

TABLE 2

Crush strength of the catalyst prepared using method in Example 2

| | Example 2 | | | |
|---|---|---|---|---|
| | Min value | Average value | Maximum value | Std Dev |
| Nominal Dia (mm) | 2.87 | 3.23 | 3.45 | 0.15 |
| Crushing Dia (mm) | 2.68 | 3.04 | 3.32 | 0.18 |
| Crush Strength (daN) | 3.19 | 5.58 | 10.90 | 1.80 |
| Slope (daN/mm) | 6.90 | 48.16 | 109.04 | 32.44 |
| Crushing strength (daN/mm) | 0.30 | 0.69 | 1.18 | 0.21 |
| Force rate (daN/s) | 0.07 | 0.48 | 1.09 | 0.32 |

As shown in Tables 1 and 2, the crush strength of the rare earth containing-catalysts is higher than the catalysts that do not contain rare earth element. The average increase in crush strength is about 41%.

Activity Test for the Catalysts

The dehydrogenation activity of the catalysts was measured in a tubular fixed-bed quartz reactor. Catalyst loading and reactor details were as follows: Catalyst weight was 5 g, catalyst particle size was 0.4-0.5 mm, reactor inner diameter was 16 mm, reactor outer diameter was 19 mm.

Isobutane (99.9 vol. %) was used as the feedstock. Quartz chips having a size of 1-1.4 mm were loaded above the catalyst bed. A nitrogen purge was employed between the steps of dehydrogenation, catalyst regeneration/oxidation, and reduction with hydrogen. The total feed flow in the dehydrogenation step corresponds to Gas Hourly Space Velocity (GHSV) of 600 mlh$^{-1}$g$^{-1}$. The reactor outlet gases were analyzed by online gas chromatograph (Agilent 6890) equipped with a flame ionization detector for hydrocarbon analysis and thermal conductivity detector for hydrogen analysis. The reactant and products flow rates were measured using a Ritter type wet gas flow meter.

The reactor was operated at atmospheric pressure and in a cyclic mode with the following steps: 1) oxidize in air at 650° C. for 30 min.; 2) purge with nitrogen at 650° C. for 10 min.; 3) reduce with H$_2$ at 650° C. for 6 min.; 4) cool under nitrogen from 650° C. to 585° C., then hold at 585° C. for 40 min.; 5) dehydrogenate isobutane at 585° C. for 21 min.; and 6) analyze with gas chromatograph (GC) at 20th minute from the start of the isobutane feed. Steps 1 to 6 were repeated several times.

Stability Test for the Catalysts

Catalyst stability evaluation was carried out by an artificial accelerated aging procedure in a cyclic mode of operation. The cycle consisted of hydrogen-isobutane-air passing stages separated by different time intervals. The aging was carried out at 820° C. for 72 hours and the second aging was carried out at 820° C. for 48 hours. Catalyst stability evaluation parameters included a catalyst weight of 5 g, isobutane GHSV of 400 ml g$^{-1}$ h$^{-1}$ and air to isobutane volume ratio of 4. The following steps were performed: 1) oxidize under air for 15 min.; 2) purge with nitrogen for 3 min.; 3) reduce with H$_2$ for 6 min.; 4) purge with nitrogen for 3 min.; 5) iso-butane flow for 3 min.; 6) purge with nitrogen for 3 min.

Results of Activity and Stability Test for the Catalysts

Comparison of Yields

Figure 3:
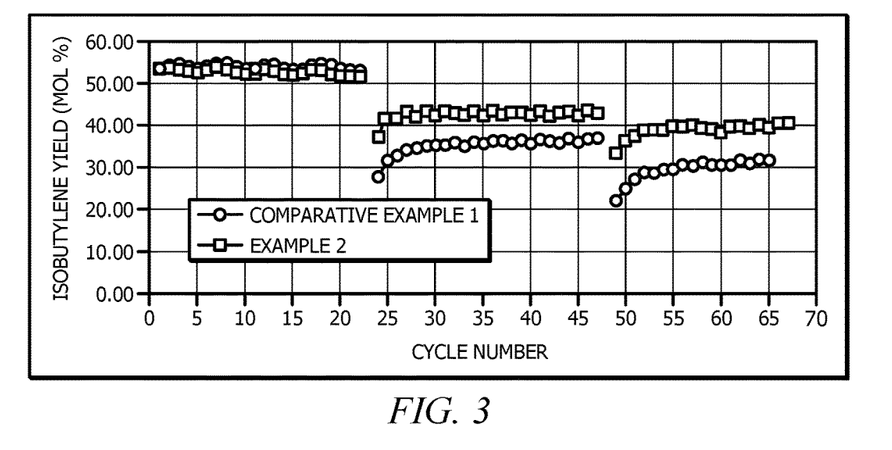
FIG. 3 shows comparison of isobutylene yields when the dehydrogenation of isobutane is performed using a conventional catalyst and a catalyst (of example 2) according to embodiments of the invention.

As depicted in FIG. 3, the two types of catalysts (comparative example 1 having no rare earth metal and example 2 having the rare earth metal-containing compound lanthanum oxide) exhibited comparable isobutylene yield over the first 22 cycles. The catalysts that were aged using the artificial accelerated aging procedure showed a marked difference in isobutylene yield. Catalysts from example 2 (catalyst having the rare earth metal-containing compound lanthanum oxide) exhibited greater than 40% isobutylene yield over cycles 24-47. During the same cycle period, catalysts from example 1 (no rare earth metal) exhibited about 36% yield. The difference in yields was even more significant over cycles 49-65. During this period, the lanthanum oxide containing catalyst (example 2) exhibited an isobutylene yield greater than 33%. The results indicate that the catalyst prepared using eta-alumina modified with lanthanum oxide was more stable in comparison to the catalyst without modification.

Comparison of Selectivity

Figure 4:
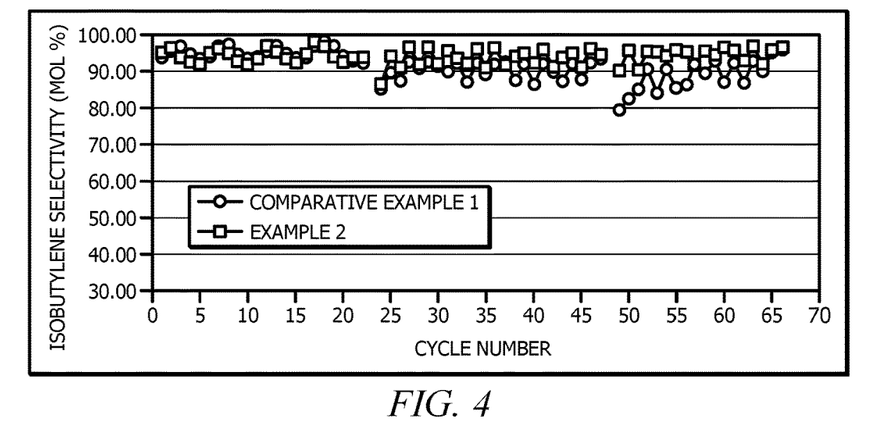
FIG. 4 shows comparison of isobutane to isobutylene selectivities between using a conventional catalyst and using a catalyst (of example 2) according to embodiments of the invention.

As depicted in FIG. 4, the two types of catalysts (comparative example 1 having no rare earth metal and example 2 having the rare earth metal-containing compound lanthanum oxide) resulted in similar isobutylene selectivities over the first 22 cycles. After the artificial accelerated aging process, the catalysts' selectivities began to diverge moderately. Catalysts from example 2 (catalyst having the rare earth metal-containing compound lanthanum oxide) exhibited marginally improved isobutylene selectivity over cycles 24-47. The difference in selectivities increased over cycles 49-65. The lanthanum oxide containing catalyst (example 2) exhibited an isobutylene selectivity of about 93%, in comparison to the catalyst lacking lanthanum oxide (comparative example 1) selectivity of about 89%. The selectivity results demonstrate that the catalyst having the rare earth metal-containing compound lanthanum oxide exhibited improved performance over time in comparison to the catalyst without lanthanum oxide.

Example 4

(A Rare Earth Metal-Containing Catalyst)

Catalyst preparation: The catalyst was prepared by impregnation using eta-alumina extrudates as alumina support. The eta-alumina extrudates were prepared by the following procedure. Bayerite (Pural-BT, Sasol) material was extrudated using nitric acid as a peptizing agent. To bayerite powder (800 g) placed in sigma kneader was dry mixed at around 45 rpm for 5 to 10 minutes and then 44.8 ml of deionized water was added randomly to the kneader drop by drop taking a time of 10 to 15 minutes. Then 160 ml of 37 vol. % nitric acid was added dropwise and the mixture was mixed for about 30 minutes. After this 2.64 g of hydroxyl propyl methyl cellulose (HPMC) was added slowly in portions and the kneading was continued for additional 20 to 30 minutes. The obtained dough was then extruded using a lab extruder (Sunsai), with dies having circular opening of 3.5 mm in diameter. The obtained extrudates were then kept at 25° C. for two hours. The extrudates were then placed in an oven at 70° C. for 30 minutes and then cooled to 25° C. and kept for 12 hours and again placed in an oven at 70° C. for 12 hours. The extrudates were then cooled to 25° C., separated and broken to 6 to 8 mm length. These extrudates were then dried at 90° C. and 120° C. for 12 hours each. Then, 450 g of dried extrudate placed in fixed bed tubular reactor and calcined at 550° C. in air for 3 hours with air flow (ml/min) equal to the volume of alumina extrudates. The calcined alumina extrudates after cooling to room temperature, was used for catalyst preparation. The impregnation solution was prepared by the following procedure. An aqueous solution of chromic acid was prepared by dissolving 451 g of $CrO_3$ in 400 ml of water. Then 14 g of lanthanum oxide was dissolved in chromic acid solution by slow addition with mixing. Then, an aqueous solution of sodium hydroxide was prepared by dissolving 18 g of sodium hydroxide in 40 ml of water and was then added to the chromic acid solution containing lanthanum oxide. An additional 55 ml of water was added to the above solution and mixed well. The impregnation is carried out using a double cone blender. The eta-alumina extrudates (1000 g, 3.2 mm×6-8 mm) was placed in a double cone blender. Under rotation of double cone blender (15 rpm), the impregnation solution was added to the blender over a period of 2 hours using a peristatic pump along with airflow. After impregnation the blender was allowed to rotate at 15 rpm for 1 hour. Then the blender was rotated at 15 rpm under air blow for 15 hours. After 15 hours, the blender rotation and air blow was stopped and the chromic acid impregnated extrudates were unloaded in a glass trays and dried at 70° C. for 12 hours. The impregnated alumina extrudates were then dried at 120° C. for 15 hours. The dried material is calcined by loading 500 g of dried impregnated material in fixed bed quartz tubular reactor. The catalyst was calcined at 650° C. for 2 hours under airflow (1375 ml/min) and then at 750° C. for 4 hours in presence of 13 volume % steam and 87 volume % air (with total flow of 1575 ml/min).

Crush strength test of the catalyst: The radial crush strength of the catalysts prepared in Example 4 was measured. About 50 g of catalyst was dried for 2 hours in an oven at 300° C. After cooling the catalysts in a desiccator, 30 extrudates were used. Each extrudate was subjected to an increasing load up to breaking point. The force applied to the extrudate at the moment of break is determined in decanewton (daN) and the results for the crush strength are expressed in daN/mm. The average crush strength of the catalyst was found to be 1.5 dN/mm.

Activity test for the catalyst: The dehydrogenation activity of the catalysts was measured in a tubular fixed-bed quartz reactor. Catalyst loading and reactor details were as follows: Catalyst weight was 5 g, catalyst particle size was 0.4-0.5 mm, reactor inner diameter was 16 mm, reactor outer diameter was 19 mm.

Isobutane (99.9 vol. %) was used as the feedstock. Quartz chips having a size of 1-1.4 mm were loaded above the catalyst bed. A nitrogen purge was employed between the steps of dehydrogenation, catalyst regeneration/oxidation, and reduction with hydrogen. The total feed flow in the dehydrogenation step corresponds to Gas Hourly Space Velocity (GHSV) of 600 $mlh^{-1}g^{-1}$. The reactor outlet gases were analyzed by online gas chromatograph (Agilent 6890) equipped with a flame ionization detector for hydrocarbon analysis and thermal conductivity detector for hydrogen analysis. The reactant and products flow rates were measured using a Ritter type wet gas flow meter.

Figures 5A, 5B:
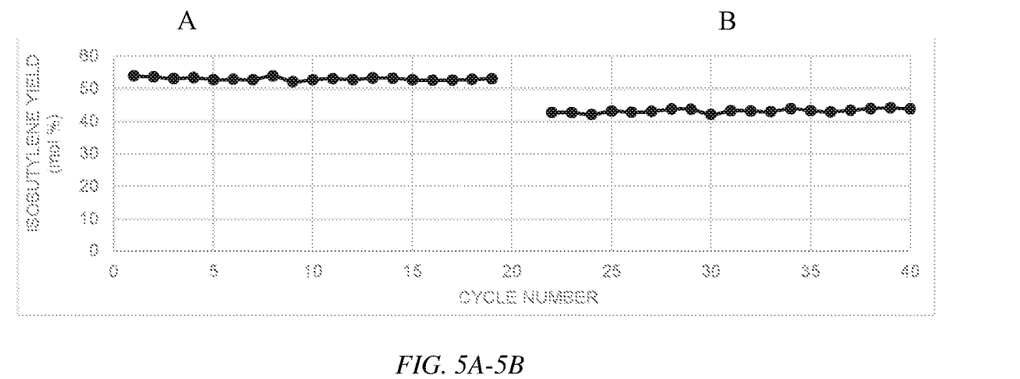
FIG. 5 shows isobutylene yields when the dehydrogenation of isobutane is performed using a catalyst (of example 4) according to embodiments of the invention, before (A) and after (B) the first aging of the catalyst, as described in Example 4.
Figures 6A, 6B:
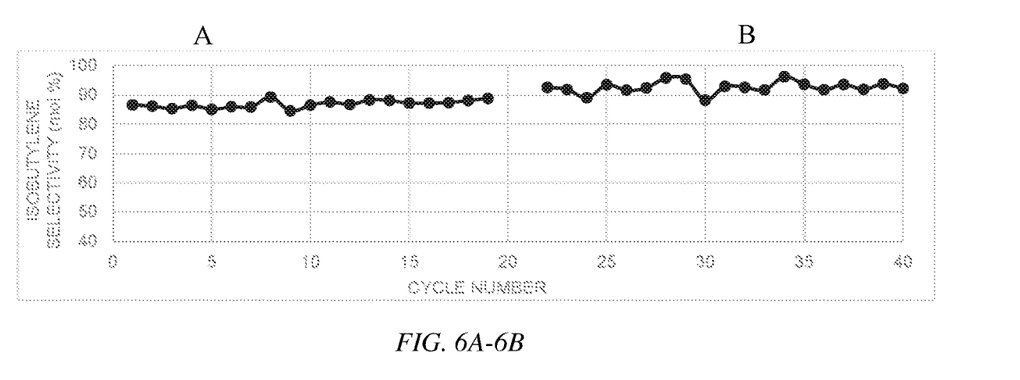
FIG. 6 shows isobutane to isobutylene selectivities using a catalyst (of example 4) according to embodiments of the invention, before (A) and after (B) the first aging of the catalyst, as described in Example 4.

The reactor was operated at atmospheric pressure and in a cyclic mode with the following steps: 1) oxidize in air at 650° C. for 30 min.; 2) purge with nitrogen at 650° C. for 10 min.; 3) reduce with $H_2$ at 650° C. for 6 min.; 4) cool under nitrogen from 650° C. to 585° C., then hold at 585° C. for 40 min.; 5) dehydrogenate isobutane at 585° C. for 21 min.; and 6) analyze with gas chromatograph (GC) at 20th minute from the start of the isobutane feed. Steps 1 to 6 were repeated several times Stability test for the catalyst: Catalyst stability evaluation was carried out by an artificial accelerated aging procedure in a cyclic mode of operation. The cycle consisted of hydrogen-isobutane-air passing stages separated by different time intervals. The aging was carried out at 820° C. for 72 hours and the second aging was carried out at 820° C. for 48 hours. Catalyst stability evaluation parameters included a catalyst weight of 5 g, isobutane GHSV of 400 ml $g^{-1}$ $h^{-1}$ and air to isobutane volume ratio of 4. The following steps were performed: 1) oxidize under air for 15 min.; 2) purge with nitrogen for 3 min.; 3) reduce with $H_2$ for 6 min.; 4) purge with nitrogen for 3 min.; 5) iso-butane flow for 3 min.; 6) purge with nitrogen for 3 min. The isobutylene yield and isobutylene selectivity of the catalyst before and after first aging is given in FIG. 5 and FIG. 6 respectively.

In the context of the present invention, at least the following 34 embodiments are described. Embodiment 1 is a paraffin dehydrogenation catalyst having improved crush strength. The paraffin dehydrogenation catalyst is produced by a process including: (a) providing a rare earth element modified alumina support in eta-alumina form, theta-alumina form, or combinations thereof; (b) impregnating the rare earth element modified alumina support with a chromium-containing solution to produce a second support; (c) drying the second support to obtain the third support; and (d) calcining the third support to obtain the paraffin dehydrogenation catalyst, wherein the paraffin dehydrogenation catalyst has a crush strength greater than about 0.4 daN/mm, and further wherein the paraffin dehydrogenation catalyst contains a rare earth metal oxide in a range of 0.5-5 wt. %. Embodiment 2 is the catalyst of embodiment 1, wherein the providing in step (a) includes: (e) providing an eta-alumina support; (f) impregnating the eta-alumina support with a rare earth element compound-containing solution to produce a first support; and (g) drying the first support and calcining the dried first support to obtain a rare earth element modified alumina support in eta-alumina form, theta-alumina form, or combination thereof. Embodiment 3 is the catalyst of embodiment 2, wherein the calcining at step (g) is performed at a calcination temperature of 700 to 1000° C. Embodiment 4 is the catalyst of embodiment 1, wherein the providing in step (a) includes: (h) providing a precursor of an eta-alumina support; (i) contacting the precursor with a rare earth compound to produce a contacted precursor; (j) shaping the contacted precursor of an eta-alumina support to produce shaped contacted precursor; and (k) drying the shaped contacted precursor and calcining the dried contacted precursor to produce the rare earth element modified support in eta-alumina form, theta-alumina form, or combinations thereof. Embodiment 5 is the catalyst of embodiment 4, wherein the precursor of an eta-alumina support includes bayerite, RHO alumina, gel alumina, or combinations thereof. Embodiment 6 is the catalyst of either of embodiments 4 or 5, wherein the shaping in step (j) includes extrusion. Embodiment 7 is the catalyst of any of embodiments 4 to 6, wherein the calcining at step (k) is performed at a calcination temperature of 700 to 1000° C. Embodiment 8 is the catalyst of any of embodiments 4 to 7, wherein the rare earth element-containing compound includes a lanthanum compound, a cerium compound, a neodymium compound, or combinations thereof. Embodiment 9 is the catalyst of any of embodiments 1 to 8, wherein the chromium-containing solution contains alkali metal hydroxide, alkali metal chromate, alkali metal dichromate, or combinations thereof. Embodiment 10 is the catalyst of any of embodiments 1 to 9, wherein the calcining at step (d) is performed at a calcination temperature of 650 to 850° C. or 700 to 850° C. Embodiment 11 is the catalyst of any of embodiments 1 to 10, wherein the paraffin dehydrogenation catalyst contains 5 to 30 wt. % or 13 to 28 wt. % of chromium and 0.1 to 5 wt. % or 0.4 to 4.3 wt. % of the rare earth element. Embodiment 12 is the catalyst of any of embodiments 1 to 11, wherein the paraffin dehydrogenation catalyst has a surface area in a range of 60 to 120 $m^2/g$.

Embodiment 13 is a method for dehydrogenating a lower paraffin. The method includes providing the paraffin dehydrogenation catalyst according to any of embodiments 1 to 12. The method further includes placing the paraffin dehydrogenation catalyst in a reactor and reacting the lower paraffin in the presence of the paraffin dehydrogenation catalyst under reaction conditions sufficient to dehydrogenate the lower paraffin. Embodiment 14 is the method of embodiment 13, wherein the lower paraffin contains propane, butane, pentane, or combinations thereof. Embodiment 15 is the method of either of embodiments 13 or 14, wherein the reactor includes a fixed bed reactor. Embodiment 16 is the method of any of embodiments 13 to 15, wherein the reaction conditions include a reaction temperature of 400 to 800° C.

Embodiment 17 is a method for producing a catalyst. The method includes: (a) contacting an eta-alumina precursor with at least one rare earth additive to provide an contacted eta-alumina precursor; (b) heating the contacted eta-alumina precursor to yield rare earth-modified eta-alumina, theta-alumina, or combination thereof; (c) impregnating the rare earth-modified alumina with a chromium compound; and (d) heating the chromium-impregnated alumina to yield the catalyst. Embodiment 18 is the method of embodiment 17, wherein the step of impregnating with a chromium compound includes impregnating to a chromium compound loading of up to 50%. Embodiment 19 is the method of either of embodiments 17 or 18, wherein the step of impregnating with a chromium compound further includes impregnating with at least one alkali metal compound. Embodiment 20 is the method of embodiment 19, wherein the at least one alkali metal compound contains a sodium compound, potassium compound, rubidium compound, cesium compound, or a combination thereof. Embodiment 21 is the method of any of embodiments 17 to 20, wherein the method to produce the catalyst further includes a shaping step. Embodiment 22 is the method of embodiment 21, wherein the eta-alumina precursor is contacted with the at least one rare earth additive before the shaping step. Embodiment 23 is the method of any of embodiments 17 to 22, wherein the heating step includes a drying step and a calcining step.

Embodiment 24 is a method for producing a catalyst. The method includes: (a) impregnating eta-alumina, theta-alumina, or a combination thereof with at least one rare earth additive and at least one chromium compound; and (b) heating the impregnated alumina to yield the catalyst. Embodiment 25 is the method of embodiment 24, wherein the step of impregnating includes impregnating to a chromium compound loading of up to 50%. Embodiment 26 is the method of embodiment 24, wherein the step of impregnating further includes impregnating with at least one alkali metal compound. Embodiment 27 is the method of embodiment 25, wherein at least one alkali metal compound contains a sodium compound, potassium compound, rubidium compound, cesium compound, or a combination thereof. Embodiment 28 is the method of any of embodiments 24 to 27, wherein the method further includes a shaping step.

Embodiment 29 is a method for producing a catalyst. The method includes: (a) treating a combination of a rare earth additive and eta-alumina with heat to provide rare earth-modified eta-alumina, theta-alumina, or combination thereof; (b) impregnating the rare earth-modified alumina with a chromium compound; and (c) heating the impregnated alumina to yield the catalyst. Embodiment 30 is the method of embodiment 29, wherein the step of impregnating with a chromium compound includes impregnating to a chromium compound loading of up to 50%. Embodiment 31 is the method of either of embodiments 29 or 30, wherein the step of impregnating with a chromium compound further includes impregnating with at least one alkali metal compound. Embodiment 32 is the method of embodiment 31, wherein the at least one alkali metal compound includes a sodium compound, potassium compound, rubidium compound, cesium compound, or a combination thereof. Embodiment 33 is the method of any of embodiments 29 to 32, wherein the method further includes a shaping step.

Embodiment 34 is a catalyst for the dehydrogenation of paraffins. The catalyst includes a support containing eta-alumina, theta-alumina, or a combination thereof. The catalyst further includes from 0.1 to 10 wt. % of at least one rare earth metal component. The catalyst still further includes from 0.1 to 5 wt. % of at least one alkali metal component. The catalyst also includes from 5 to 40 wt. % of a chromium component, wherein the catalyst weight balance is eta-alumina, theta-alumina, or a combination thereof.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A paraffin dehydrogenation catalyst having improved crush strength produced by a process comprising:
   (a) providing a rare earth element modified alumina support in eta-alumina form comprising a rare earth element-containing compound comprising a rare earth element by:
      (i) providing an eta-alumina support;
      (ii) impregnating the eta-alumina support with a rare earth element compound containing solution to produce a first support; and
      (iii) drying the first support and calcining the dried first support to obtain the rare earth element modified alumina support in eta-alumina form;

(b) impregnating the rare earth element modified alumina support with a chromium-containing solution to produce a second support;
(c) drying the second support to obtain the third support;
(d) calcining the third support to obtain the paraffin dehydrogenation catalyst; wherein the paraffin dehydrogenation catalyst has a crush strength greater than about 0.4 daN/mm, and further wherein the paraffin dehydrogenation catalyst contains 0.5 to 5 wt. % of a rare earth metal oxide, 30 to 40 wt. % of chromium (III) oxide, 0.1 to 5 wt. % of at least one alkali metal component, and the balance the eta-alumina; and wherein the at least one alkali metal component comprises a sodium compound, potassium compound, rubidium compound, cesium compound, or a combination thereof.

2. The catalyst of claim 1, wherein the calcining at step (g) is performed at a calcination temperature of 700 to 1000° C.

3. The catalyst of claim 1, wherein the providing in step (a) comprises:
(h) providing a precursor of an eta-alumina support;
(i) contacting the precursor with a rare earth element-containing compound containing solution to produce a contacted precursor;
(j) shaping the contacted precursor to produce shaped contacted precursor;
(k) drying the shaped contacted precursor to produce a dried contacted precursor and calcining the dried contacted precursor to produce the rare earth element modified support in eta-alumina form.

4. The catalyst of claim 3, wherein the precursor of an eta-alumina support includes bayerite, RHO alumina, gel alumina, or combinations thereof.

5. The catalyst of claim 3, wherein the shaping in step (j) comprises extrusion.

6. The catalyst of claim 3, wherein the calcining at step (k) is performed at a calcination temperature of 700 to 1000° C.

7. The catalyst of claim 3, wherein the rare earth element-containing compound includes a lanthanum compound, a cerium compound, a neodymium compound, or combinations thereof.

8. The catalyst of claim 1, wherein the chromium-containing solution comprises alkali metal hydroxide, alkali metal chromate, alkali metal dichromate, or combinations thereof.

9. The catalyst of claim 1, wherein the calcining at step (d) is performed at a calcination temperature of 650 to 850° C.

10. The catalyst of claim 1, wherein the paraffin dehydrogenation catalyst has a surface area in a range of 60 to 120 m$^2$/g.

11. A method for producing a paraffin dehydrogenation catalyst, the method comprising the steps of:
(a) providing a rare earth element modified alumina support in eta-alumina form comprising a rare earth element-containing compound comprising a rare earth element by:
(i) providing an eta-alumina support;
(ii) impregnating the eta-alumina support with a rare earth element compound containing solution to produce a first support; and
(iii) drying the first support and calcining the dried first support to obtain the rare earth element modified alumina support in eta-alumina form;
(b) impregnating the rare earth element modified alumina support with a chromium-containing solution to produce a second support;
(c) drying the second support to obtain the third support;
(d) calcining the third support to obtain the paraffin dehydrogenation catalyst;
wherein the paraffin dehydrogenation catalyst has a crush strength greater than about 0.4 daN/mm,
wherein the paraffin dehydrogenation catalyst contains 0.5 to 5 wt. % of a rare earth metal oxide, 17 to 40 wt. % of chromium (III) oxide, 0.1 to 5 wt. % of at least one alkali metal component, and the balance the eta-alumina; and
wherein the at least one alkali metal component comprises a sodium compound, potassium compound, rubidium compound, cesium compound, or a combination thereof.

12. The method of claim 11, wherein the method to produce the catalyst further comprises a shaping step.

* * * * *